US010821122B2

(12) United States Patent
Ahmed et al.

(10) Patent No.: US 10,821,122 B2
(45) Date of Patent: *Nov. 3, 2020

(54) HYDROGEN SULPHIDE COMPOUNDS

(71) Applicant: Aston University, West Midlands (GB)

(72) Inventors: Asif Ahmed, West Midlands (GB); Keqing Wang, West Midlands (GB)

(73) Assignee: ASTON UNIVERSITY, Birmingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/229,173

(22) Filed: Dec. 21, 2018

(65) Prior Publication Data
US 2019/0328756 A1 Oct. 31, 2019

Related U.S. Application Data

(63) Continuation of application No. 14/771,285, filed as application No. PCT/GB2014/050608 on Mar. 3, 2014, now Pat. No. 10,195,220.

(30) Foreign Application Priority Data

Mar. 1, 2013 (GB) .................. 1303649.6

(51) Int. Cl.
A61K 31/675 (2006.01)
A61K 31/095 (2006.01)

(52) U.S. Cl.
CPC .......... A61K 31/675 (2013.01); A61K 31/095 (2013.01)

(58) Field of Classification Search
USPC ......................................................... 514/90
See application file for complete search history.

(56) References Cited

U.S. PATENT DOCUMENTS

| | | | |
|---|---|---|---|
| 8,361,514 B2 | 1/2013 | Gojon-Romanillos | |
| 10,195,220 B2* | 2/2019 | Ahmed | A61K 31/095 |
| 2001/0056068 A1 | 12/2001 | Chwalisz | |
| 2012/0040371 A1 | 2/2012 | Buhimschi | |
| 2012/0077878 A1 | 3/2012 | Berner | |
| 2016/0012902 A1 | 5/2016 | Ahmed et al. | |

FOREIGN PATENT DOCUMENTS

| | | |
|---|---|---|
| JP | 2006151861 | 6/2006 |
| WO | 2004/073623 | 9/2004 |
| WO | 2011161436 | 12/2011 |
| WO | 2016/132136 | 8/2016 |
| WO | 20160132136 | 8/2016 |

OTHER PUBLICATIONS

Rossoni, European Journal of Pharmacology (2010), 648(1-3), 139-145.*
Tao, Zhongguo Yikan (2005), 40(1), 39-41.*
Hodges, American Journal of Obstetrics & Gynecology Supplement to Jan. 2012.*
Patel, Reproductive biology and endocrinology : RB&E (2009), 7, 10.*
Pan, Zhongguo Yaolixue Tongbao (2010), 26(3), 302-304.*
Zhao W, Zhang J, Lu Y, Wang R. The vasorelaxant effect of H(2)S as a novel endogenous gaseous K(ATP) channel opener. Embo J. 2001;20(21):6008-6016.
Papapetropoulos A, Pyriochou A, Altaany Z, Yang G, Marazioti A, Zhou Z, Jeschke MG, Branski LK, Herndon DN, Wang R, Szabo C. Hydrogen sulfide is an endogenous stimulator of angiogenesis. Proc Natl Acad Sci U S A. 2009;106(51):21972-21977.
Zanardo RC, Brancaleone V, Distrutti E, Fiorucci S, Cirino G, Wallace JL. Hydrogen sulfide is an endogenous modulator of leukocyte-mediated inflammation. Faseb J. 2006;20(12):2118-2120.
Blackstone E, Roth MB. Suspended animation-like state protects mice from lethal hypoxia. Shock. 2007;27(4):370-372.
Elrod JW, Calvert JW, Morrison J, Doeller JE, Kraus DW, Tao L, Jiao X, Scalia R, Kiss L, Szabo C, Kimura H, Chow CW, Lefer DJ. Hydrogen sulfide attenuates myocardial ischemia-reperfusion injury by preservation of mitochondrial function. Proc Natl Acad Sci U S A. 2007;104(39)1 5560-15565.
Kabil O, Vitvitsky V, Xie P, Banerjee R. The quantitative significance of the transsulfuration enzymes for H2S production in murine tissues. Antioxid Redox Signal. 2011;15(2):363-372.
Ramma W, Buhimschi IA, Zhao G, Dulay AT, Nayeri UA, Buhimschi CS, Ahmed A. The elevation in circulating anti-angiogenic factors is independent of markers of neutrophil activation in preeclampsia. Angiogenesis. 2012;15(3):333-340.
Lee M, J. Effects of Hydrogen Sulfide-releasing L-DOPA Derivatives on Glial Activation. Biol Chem (2010) 285, 17318-17328.
Ahmad S, Ahmed A. Elevated placental soluble vascular endothelial growth factor receptor-1 inhibits angiogenesis in preeclampsia. Circ Res. 2004;95(9):884-891.
Predmore B.L. et al.Hydrogen Sulfide in Biochemistry and Medicine (Antioxidants and Redox Signalling (2012) 17 (1) 119-140).
Banerjee R. Hydrogen sulfide: redox metabolism and signaling. Antioxid Redox Signal. 2011;15(2):339-341.
Hogberg U. The World Health Report 2005: "make every mother and child count"—including Africans. Scand J Public Health. 2005;33(6):409-411.
Bannenberg G.L. and Viera HLA. Therapeutic applications of the gaseous mediators carbon monoxide and hydrogen sulfide. (Expert Opin. Ther. Patents (2009) 19(5) 663-682).
Thadhani R, Mutter WP, Wolf M, Levine RJ, Taylor RN, Sukhatme VP, Ecker J, Karumanchi SA. First trimester placental growth factor and soluble fms-like tyrosine kinase 1 and risk for preeclampsia. J Clin Endocrinol Metab. 2004;89(2):770-775.

(Continued)

Primary Examiner — Nizal S Chandrakumar

(74) Attorney, Agent, or Firm — Brannon Sowers & Cracraft PC

(57) ABSTRACT

The application describes Hydrogen Sulphide ($H_2S$), or a ($H_2S$) generating compound or compound capable of stimulating $H_2S$ production in a pregnant subject, for use in the treatment of pre-eclampsia (PE) or fetal growth restriction.

20 Claims, 8 Drawing Sheets

Figure 1:
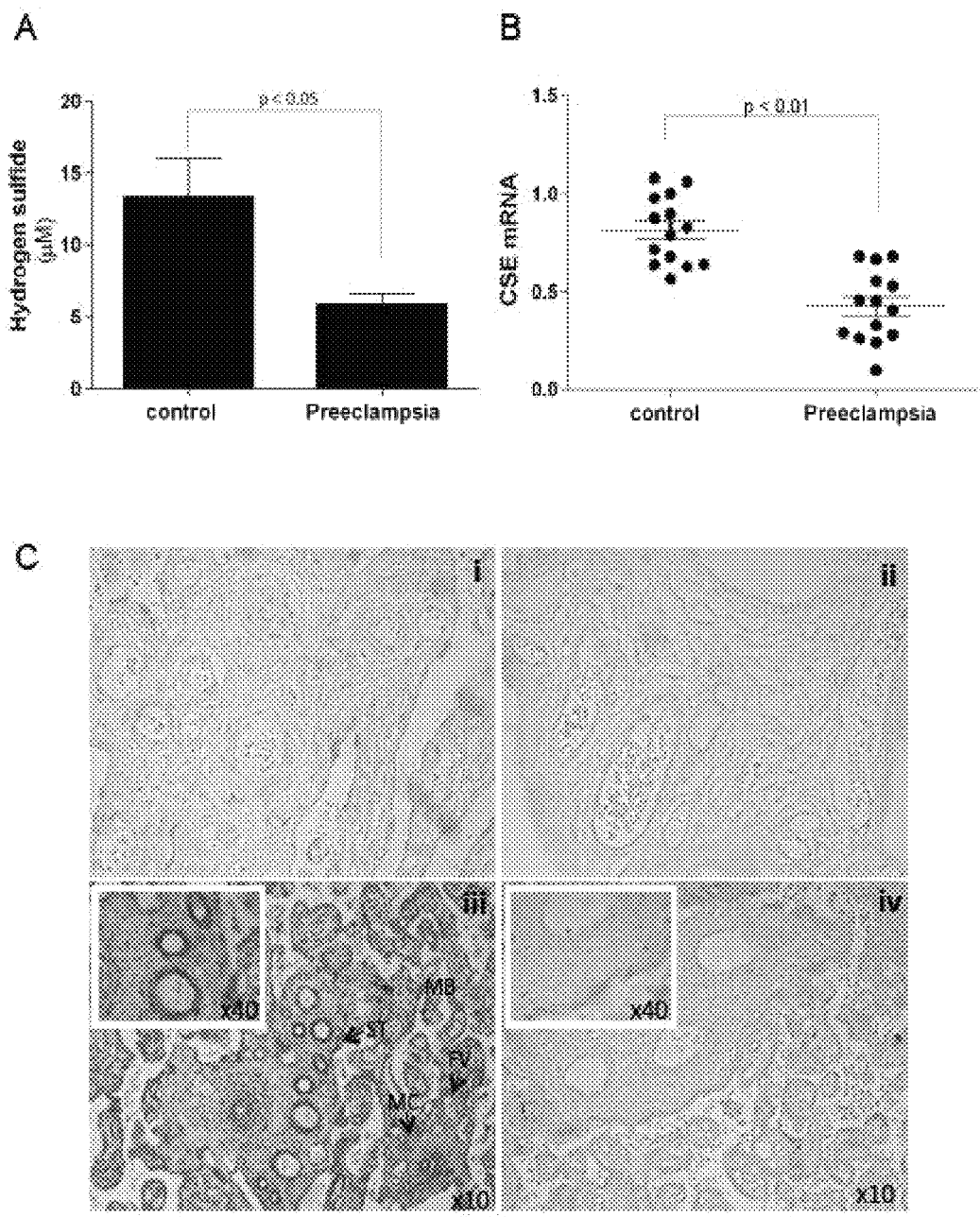

Specification includes a Sequence Listing.

(56) References Cited

OTHER PUBLICATIONS

Egbor M, Ansari T, Morris N, Green CJ, Sibbons PD. Morphometric placental villous and vascular abnormalities in early- and late-onset pre-eclampsia with and without fetal growth restriction. *Bjog.* 2006;113(5):580-589.

Ahmed A, Cudmore MJ. Can the biology of VEGF and haem oxygenases help solve pre-eclampsia? *Biochem Soc Trans.* 2009;37(Pt 6):1237-1242.

Maynard SE, Karumanchi SA. Angiogenic factors and preeclampsia. *Semin Nephrol.* 2011;31(1):33-46.

Levine RJ, Maynard SE, Qian C, Lim KH, England LJ, Yu KF, Schisterman EF, Thadhani R, Sachs BP, Epstein FH, Sibai BM, Sukhatme VP, Karumanchi SA. Circulating angiogenic factors and the risk of preeclampsia. *N Engl J Med.* 2004;350(7):672-683.

Levine RJ, Lam C, Qian C, Yu KF, Maynard SE, Sachs BP, Sibai BM, Epstein FH, Romero R, Thadhani R, Karumanchi SA. Soluble endoglin and other circulating antiangiogenic factors in preeclampsia. *N Engl J Med.* 2006;355(10):992-1005.

Chen CP. Placental abnormalities and preeclampsia in trisomy 13 pregnancies. *Taiwan J Obstet Gynecol.* 2009;48(1):3-8.

Ramma W, Ahmed A. Is inflammation the cause of pre-eclampsia? *Biochem Soc Trans.* 2011;39(6):1619-1627.

Saxena AR, Karumanchi SA, Brown NJ, Royle CM, McElrath TF, Seely EW. Increased sensitivity to angiotensin II is present postpartum in women with a history of hypertensive pregnancy. *Hypertension.* 2010;55(5):1239-1245.

Damsky CH, Fitzgerald ML, Fisher SJ. Distribution patterns of extracellular matrix components and adhesion receptors are intricately modulated during first trimester cytotrophoblast differentiation along the invasive pathway, in vivo. *J Clin Invest.* 1992;89(1):210-222.

Savvidou MD, Noori M, Anderson JM, Hingorani AD, Nicolaides KH. Maternal endothelial function and serum concentrations of placental growth factor and soluble endoglin in women with abnormal placentation. *Ultrasound Obstet Gynecol.* 2008;32(7):871-876.

Foidart JM, Munaut C, Chantraine F, Akolekar R, Nicolaides KH. Maternal plasma soluble endoglin at 11-13 weeks' gestation in pre-eclampsia. *Ultrasound Obstet Gynecol.* 2010;35(6):680-687.

Cudmore M, Ahmad S, Al-Ani B, Fujisawa T, Coxall H, Chudasama K, Devey LR, Wigmore SJ, Abbas A, Hewett PW, Ahmed A. Negative regulation of soluble Flt-1 and soluble endoglin release by heme oxygenase-1. *Circulation.* 2007;115(13):1789-1797.

Cross JC, Simmons DG, Watson ED. Chorioallantoic morphogenesis and formation of the placental villous tree. *Ann N Y Acad Sci.* 2003;995:84-93.

You XJ, Xu C, Lu JQ, Zhu XY, Gao L, Cui XR, Li Y, Gu H, Ni X. Expression of cystathionine beta-synthase and cystathionine gamma-lyase in human pregnant myometrium and their roles in the control of uterine contractility. *PLoS ONE.* 2011;6(8):e23788.

Costantine, Maged M., and Kirsten Cleary. "Pravastatin for the prevention of preeclampsia in highrisk pregnant women." *Obstetrics and gynecology* 121.2 0 1 (2013).

Olson, Kenneth R. "The therapeutic potential of hydrogen sulfide: separating hype from hope." *American Journal of Physiology-Regulatory, Integrative and Comparative Physiology* 301.2 (2011): R297-R312.

Robinson, Hayley, and Susan Wray. "A new slow releasing, H2S generating compound, GYY4137 relaxes spontaneous and oxytocin-stimulated contractions of human and rat pregnant myometrium." *PloS one* 7.9 (2012): e46278.

Yu, J., et al. "Effects of SAC on oxidative stress and NO availability in placenta: potential benefits to preeclampsia." *Placenta* 33.6 (2012): 487-494.

Cindrova-Davies, Tereza, et al. "Reduced cystathionine y-lyase and increased miR-21 expression are associated with increased vascular resistance in growth-restricted pregnancies: hydrogen sulfide as a placental vasodilator." *The American journal of pathology* 182.4 (2013): 1448-1458.

Holwerda, K. M., et al. "Hydrogen sulfide producing enzymes in pregnancy and preeclampsia." *Placenta* 33.6 (2012): 518-521.

Holwerda, Kim M., et al. "Gasotransmitters: a solution for the therapeutic dilemma in preeclampsia?." *Hypertension* 62.4 (2013): 653-659.

PCT Search Report prepared for PCT/GB2014/050408, dated May 21, 2014.

Delic, Ralko, et al. "Statistical regression model of standard and new laboratory markers and its usefulness in prediction of preeclampsia." *The Journal of Maternal-Fetal & Neonatal Medicine* 27.4 (2014): abstract.

Sankaralingam, Sowndramalingam, Han Xu, and Sandra T. Davidge. "Arginase contributes to endothelial cell oxidative, tress in response to plasma from women with preeclampsia." *Cardiovascular research* 85.1 (2009): 194-203.

George, Eric M., et al. "Heme oxygenase-1 attenuates hypoxia-induced sFlt-1 and oxidative stress in placental villi through its metabolic products CO and bilirubin." *International journal of hypertension* 2012 (2011 ).

Molvarec, Attila, et al. "Circulating angiogenic factors determined by electrochemiluminescence immunoassay in 5 relation to the clinical features and laboratory parameters in women with preeclampsia." *Hypertension Research* 33.9 2010): 892-898.

Levine RJ, Thadhani R, Qian C, Lam C, Lim KH, Yu KF, Blink AL, Sachs BP, Epstein FH, Sibai BM, Sukhatme VP, Karumanchi SA. Urinary placental growth factor and risk of preeclampsia. *Jama.* 2005;293(1):77-85.

Noori M, Donald AE, Angelakopoulou A, Hingorani AD, Williams DJ. Prospective study of placental angiogenic factors and maternal vascular function before and after preeclampsia and gestational hypertension. *Circulation.* 2010;122(5):478-487.

James, P. R., & Nelson-Piercy, C. (2004). Management of hypertension before, during, and after pregnancy. Heart, 90(12), 1499-1504.

Torry DS, Wang HS, Wang TH, Caudle MR, Torry RJ. Preeclampsia is associated with reduced serum levels of placenta growth factor. *Am J Obstet Gynecol.* 1998;179(6 Pt 1):1539-1544.

Taylor RN, Grimwood J, Taylor RS, McMaster MT, Fisher SJ, North RA. Longitudinal serum concentrations of placental growth factor: evidence for abnormal placental angiogenesis in pathologic pregnancies. *Am J Obstet Gynecol.* 2003;188(1):177-182.

Buhimschi CS, Norwitz ER, Funai E, Richman S, Guller S, Lockwood CJ, Buhimschi IA. Urinary angiogenic factors cluster hypertensive disorders and identify women with severe preeclampsia. *Am J Obstet Gynecol.* 2005;192(3):734-741.

Rossoni, Giuseppe, et al. "Activity of a new hydrogen sulfide-releasing aspirin (ACS14) on pathological cardiovascular alterations induced by glutathione depletion in rats." *European journal of pharmacology* 648.1-3 (2010): 139-145.

Tao Xia, "1, Ding Ya-guang 2, Zhang Xiao-xiao 1, Li Xiao-hui 2, Zhang Chun-yu 2, Jin Hong-fang 2, Du Jun-bao# 2, Tang Chao-shu 3.(Department of Obstetric and Gynecology, First Hospital, Peking University, Beijing 100034, China); Changes in a new gaseous signal molecule, hydrogen sulfide (H _ (2S)), in patients with pregnancyinduced hypertension syndrome [J]." Chinese Journal of Medicine 1 (2005).

Hodges, Jennifer, et al. "765: Human placental expression of the hydrogen sulfide synthesizing system: effects of gestational age and preeclampsia." American Journal of Obstetrics & Gynecology 206.1 (2012): S338.

Patel, Pushpa, et al. "The endogenous production of hydrogen sulphide in intrauterine tissues." *Reproductive Biology and Endocrinology* 7.1 (2009): 10.

Pan, Ji-gang, et al. "Effects of hydrogen sulphide on the proliferation and apoptosis of human fetal lung fibroblasts during hypoxia [J]." Chinese Pharmacological Bulletin 3 (2010): 008.

Pei, Yanxi, et al. "Hydrogen sulfide mediates the anti-survival effect of sulforaphane on human prostate cancer cells." *Toxicology and applied pharmacology* 257.3 (2011): 420-428.

Ahmed, Asif. "PL15 Can Hydrogen sulfide prevent preeclampsia and fetal growth restriction?." *Nitric Oxide* 31 (2013): S17.

Wang, Keqing, et al. "Dysregulation of hydrogen sulfide (H2S) producing enzyme cystathionine γ-lyase (CSE) contributes to maternal hypertension and placental abnormalities in preeclampsia." *Circulation* (2013): CIRCULATIONAHA-113.

(56) References Cited

OTHER PUBLICATIONS

Carson, Ray J., and Justin C. Konje. "Role of hydrogen sulfide in the female reproductive tract." Expert Review of Obstetrics & Gynecology 5.2 (2010): 203-213.

PCT Search Report prepared for PCT/GB2016/050408, dated Jul. 15, 2016.

Ahmad, Shakil, et al. "Direct evidence for endothelial vascular endothelial growth factor receptor-1 function in nitric oxide-mediated angiogenesis." Circulation research 99.7 (2006): 715-722.

Tao et al. (2005) Changes in a new gaseous signalling molecule, hydrogen sulfide, in patients with pregnancy-induced hypertension syndrome. Zhongguo Yikan, vol. 40, No. 1, pp. 39-41.

Wang et al. (2013) Dysregulation of hydrogen sulfide producing enzyme cystathionine-lyase contributes to maternal hypertension and placental abnormalities in preeclampsia. Circulation, vol. 127, No. 25, pp. 2514-2522.

Agrawal, International Journal of Medicine and Public Health | Oct.-Dec. 2014 | vol. 4 | Issue 4:.350-353.

Conde-Agudelo, Agustín, et al. "Supplementation with vitamins C and E during pregnancy for the prevention of preeclampsia and other adverse maternal and perinatal outcomes: a systematic review and metaanalysis." American Journal of Obstetrics & Gynecology 204.6 (2011): 503-e1.

Communication Pursuant to Article 94(3) EPC for EP 14709393.4, dated Mar. 29, 2018.

Lely, State of the Art Lectures, Plenary Presentations and Oral Communications/ Pregnancy Hypertension 1, Supplement 1 (2010) S1-S41.

Marcoux, American Journal of Epidemiology, 1989, vol. 130, No. 5, 950-957.

Karumanchi, Hypertension. May 2010; 55(5): 1100-1101.

Dogra, Vikram S. "Imaging in Intrautering Growth Retardation." Medscape, Drugs & Diseases, Nov.

Kumasawa, Keiichi, et al. "Pravastatin induces placental growth factor (PGF) and ameliorates preeclampsia in a mouse model." *Proceedings of the National Academy of Sciences* 108.4 (2011).

Yan H, Du J, Tang C. The possible role of hydrogen sulfide on the pathogenesis of spontaneous hypertension in rats. Biochem Biophys Res Commun. 2004;313(1):22-27.

Yang G, Wu L, Jiang B, Yang W, Qi J, Cao K, Meng Q, Mustafa AK, Mu W, Zhang S, Snyder SH, Wang R. H2S as a physiologic vasorelaxant: hypertension in mice with deletion of cystathionine gamma-lyase. Science. 2008;322(5901):587-590.

Ahmad S, Hewett PW, Wang P, Al-Ani B, Cudmore M, Fujisawa T, Haigh JJ, le Noble F, Wang L, Mukhopadhyay D, Ahmed A. Direct evidence for endothelial vascular endothelial growth factor receptor-1 function in nitric oxide-mediated angiogenesis. Circ Res. 2006;99(7):715-722.

Zhuo Y, Chen PF, Zhang AZ, Zhong H, Chen CQ, Zhu YZ. Cardioprotective effect of hydrogen sulfide in ischemic reperfusion experimental rats and its influence on expression of surviving gene. Biol Pharm Bull. 2009;32(8):1406-1410.

Reynolds LP, Redmer DA. Utero-placental vascular development and placental function. J Anim Sci. 1995;73(6):1839-1851.

Maynard SE, Min JY, Merchan J, Lim KH, Li J, Mondal S, Libermann TA, Morgan JP, Sellke FW, Stillman IE, Epstein FH, Sukhatme VP, Karumanchi SA. Excess placental soluble fms-like tyrosine kinase 1 (sFlt1) may contribute to endothelial dysfunction, hypertension, and proteinuria in preeclampsia. J Clin Invest. 2003;111(5):649-658.

Wolf M, Hubel CA, Lam C, Sampson M, Ecker JL, Ness RB, Rajakumar A, Daftary A, Shakir AS, Seely EW, Roberts JM, Sukhatme VP, Karumanchi SA, Thadhani R. Preeclampsia and future cardiovascular disease: potential role of altered angiogenesis and insulin resistance. J Clin Endocrinol Metab. 2004;89(12):6239-6243.

Adamson SL, Lu Y, Whiteley KJ, Holmyard D, Hemberger M, Pfarrer C, Cross JC. Interactions between trophoblast cells and the maternal and fetal circulation in the mouse placenta. Dev Biol. 2002;250(2):358-373.

Watson ED, Cross JC. Development of structures and transport functions in the mouse placenta. Physiology (Bethesda). 2005;20:180-193.

Ohlsson R, Falck P, Hellstrom M, Lindahl P, Bostrom H, Franklin G, Ahrlund-Richter L, Pollard J, Soriano P, Betsholtz C. PDGFB regulates the development of the labyrinthine layer of the mouse fetal placenta. Dev Biol. 1999;212(1):124-136.

Tang G, Wu L, Wang R. The effect of hydroxylamine on KATP channels in vascular smooth muscle and underlying mechanisms. Mol Pharmacol. 2005;67(5):1723-1731.

Sparatore A et al.Therapeutic Potential of New Hydrogen Sulfide-releasing Hybrids. Expert Rev, Clin. Pharmacol (2011) 4, 109-121).

Holwerda, K. M., Faas, M. M., van Goor, H., & Lely, A. T. (2013). Gasotransmitters: a solution for the therapeutic dilemma in preeclampsia?. Hypertension, 62(4), 653-659.

Rossoni, G., Manfredi, B., Tazzari, V., Sparatore, A., Trivulzio, S., Del Soldato, P., & Berti, F. (2010). Activity of a new hydrogen sulfide-releasing aspirin (ACS14) on pathological cardiovascular alterations induced by glutathione depletion in rats. European journal of pharmacology, 648(1-3), 139-145.

Hodges, J., Wang, W., Lechuga, T., Laurent, L., Parast, M., & Chen, D. B. (2012). 765: Human placental expression of the hydrogen sulfide synthesizing system: effects of gestational age and preeclampsia. American Journal of Obstetrics & Gynecology, 206(1), S338.

Pei et al. {2011} Hydrogen sulfide mediates the anti-survival effect of sulforaphane on human prostate cancer cells. Toxicology and applied pharmacology, vol. 257, No. 3, pp. 420-428.

Ahmed et al. (2013) Can hydrogen sulfide prevent preeclampsia and fetal growth restriction? Nitric Oxide, vol. 31, p. S17.

Carson et al. {2010) Role of hydrogen sulfide in the female reproductive tract. Expert Reviews of Obstetrics & Gynecology, vol. 5, No. 2, pp. 203-213.

Delić, Ratko, et al. "Statistical regression model of standard and new laboratory markers and its usefulness in prediction of preeclampsia." The Journal of Maternal-Fetal & Neonatal Medicine 27.4 (2014): 388-392.

George, Eric M., et al. "Heme oxygenase-1 attenuates hypoxia-induced sFlt-1 and oxidative stress in placental villi through its metabolic products CO and bilirubin." International journal of hypertension 2012 (2011).

Sankaralingam, Sowndramalingam, Han Xu, and Sandra T. Davidge. "Arginase contributes to endothelial cell oxidative stress in response to plasma from women with preeclampsia." Cardiovascular research 85.1 (2009): 194-203.

Molvarec, Attila, et al. "Circulating angiogenic factors determined by electrochemiluminescence immunoassay in relation to the clinical features and laboratory parameters in women with pre-eclampsia." Hypertension Research 33.9 (2010): 892-898.

Holwerda KM, Bos EM, Rajakumar A, Ris-Stalpers C, van Pampus MG, Timmer A, Erwich JJ, Faas MM, van Goor H, Lely AT. Hydrogen sulfide producing enzymes in pregnancy and preeclampsia. Placenta. 2012;33(6):518-521.

Kumasawa, Keiichi, et al. "Pravastatin induces placental growth factor (PGF) and ameliorates preeclampsia in a mouse model." Proceedings of the National Academy of Sciences 108.4 (2011): 1451-1455.

Patel P, Vatish M, Heptinstall J, Wang R, Carson RJ. The endogenous production of hydrogen sulphide in intrauterine tissues. Reprod Biol Endocrinol. 2009;7:10.

Dorniak-Wall, T., Grivell, R. M., Dekker, G. A., Hague, W., & Dodd, J. M. (2014). The role of L-arginine in the prevention and treatment of pre-eclampsia: a systematic review of randomised trials. Journal of human hypertension, 28(4), 230.

Lowe, D. T. (2014). Comment on Dorniak-Wall et al.'s paper on L-arginine for pre-eclampsia. Journal of human hypertension, 28(4), 282.

Vaughan, J. E., & Walsh, S. W. (2002). Oxidative stress reproduces placental abnormalities of preeclampsia. Hypertension in pregnancy, 21(3), 205-223.

Tao, Xia, (2005). 1, Ding Ya-guang 2, Zhang Xiao-xiao 1, Li Xiao-hui 2, Zhang Chun-yu 2, Jin Hong-fang 2, Du Jun-bao# 2, Tang Chao-shu 3.(Department of Obstetric and Gynecology, First Hospital, Peking University, Beijing 100034, China); Changes in a

(56) References Cited

OTHER PUBLICATIONS new gaseous signal molecule, hydrogen sulfide (H_(2S)), in patients with pregnancyinduced hypertension syndrome [J]. Chinese Journal of Medicine. 2005.

Wang, Keqing, et al. "Dysregulation of hydrogen sulfide (H2S) producing enzyme cystathionine y-lyase (CSE) contributes to maternal hypertension and placental abnormalities in preeclampsia." Circulation Circulation, vol. 127, No. 25, pp. 2514-2522.

\* cited by examiner

A

B

HYDROGEN SULPHIDE COMPOUNDS

CROSS-REFERENCE TO RELATED APPLICATION

This application is a continuation of U.S. patent application Ser. No. 14/771,285, filed Aug. 28, 2015, which is a U.S. national application under 37 C.F.R. § 371(b) of International Application Serial No. PCT/GB2014/050608 filed Mar. 3, 2014, which claims the benefit under 35 U.S.C. § 119(a) of GB Patent Application No. 1303649.6 filed on Mar. 1, 2013, the entire disclosures of each of which are incorporated herein by reference.

The invention relates to methods of treating pre-eclampsia or impaired fetal growth and to methods of monitoring such treatment, wherein the production of hydrogen sulphide ($H_2S$) is generated or stimulated, or is provided.

Hydrogen sulphide ($H_2S$), a gaseous signaling molecule, promotes vasodilatation[1] and stimulates angiogenesis in the vasculature[2] $H_2S$ anti-inflammatory properties[3] and is also cytoprotective against cellular damage induced by lethal hypoxia or reperfusion injury.[4,5] Cystathionine γ-lyase (CSE) is the principal enzyme responsible for the endogenous production of $H_2S$.[6] Chronic administration of the CSE inhibitor DL-propargylglycine (PAG) leads to elevated blood pressure and vascular remodeling in the rat[7] and both CSE and $H_2S$ levels are reduced in pulmonary hypertensive rats.[8] Mice genetically deficient in CSE develop age-dependent hypertension, severe hyperhomocysteinaemia, and endothelial dysfunction.[9] Clearly $H_2S$ has multiple roles in health and disease,[10,11] however its role in pregnancy-induced hypertension is unknown.

Preeclampsia is a hypertensive syndrome that affects 4-7% of all pregnancies and is a major contributor to maternal and fetal morbidity and mortality worldwide.[12] It is classified as proteinuric and non-proteinuric preeclampsia.[13] While women with proteinuric preeclampsia exhibit the classic symptoms such as hypertension and proteinuria after 20 weeks gestation, women with non-proteinuric preeclampsia are more likely to suffer from hypertension and liver disease. Compare with gestational hypertension, these group of women are more likely to have intrauterine growth restriction (IUGR)[13]. The exact aetiology of preeclampsia is unknown, but there is a good association with abnormal placentation[14,15] and imbalance in angiogenic factors.[16,17] Importantly, circulating levels of soluble Flt-1 (sFlt-1), the endogenous inhibitor of vascular endothelial growth factor (VEGF) and placental growth factor (PlGF) as well as soluble endoglin (sEng), the cleaved product of the transforming growth factor β1 (TGF-β1) co-receptor Endoglin, are elevated several weeks prior to the onset of the clinical manifestations of preeclampsia,[18,19] while PlGF is reduced in the first trimester of pregnant women who subsequently developed the syndrome.[20-26] Together with endothelial dysfunction, these have become the biochemical hallmark of severe preeclampsia. Few studies have investigated the functions of CSE/$H_2S$ in pregnancy. Recently, Patel et al. demonstrated that both cystathionine β-synthase and CSE are present in human intrauterine tissues and placenta.[27,28] Given that the placenta is a highly vascular organ the inventors believe that the dysregulation of CSE/$H_2S$ pathway may contribute to placental abnormalities and a preeclampsia-like condition.

The inventors have now demonstrated that plasma $H_2S$ levels in the mother and CSE expression in the placenta are reduced in pregnancies complicated by preeclampsia as compared with gestational age matched controls. Evidence for the reduction in circulating $H_2S$ in preeclampsia is provided and which is accompanied by down-regulation of placental CSE, the key enzyme responsible for the generation of endogenous $H_2S$. Inhibition of CSE activity ex vivo placental explants from first trimester (8-12 weeks) of pregnancy result in marked decrease in placenta growth factor (PlGF) production and trophoblast invasion in vitro is inhibited. Inhibition of CSE in pregnant mice induces hypertension, increases sFlt-1 and sEng levels and causes placental abnormalities due to inhibition of $H_2S$ production as a slow releasing, $H_2S$-generating compound, GYY4137, restored fetal growth compromised by CSE inhibition and inhibited the rise in circulating sFlt-1 and sEng levels. These findings indicate that a dysfunctional CSE/$H_2S$ pathway contributes to the pathogenesis of preeclampsia.

The invention provides hydrogen sulphide ($H_2S$), a $H_2S$ generating compound or compound capable of stimulating $H_2S$ production in a pregnant subject, for use in the treatment of pre-eclampsia (PE) or fetal growth restriction (FGR or intra uterine fetal growth restriction).

The invention also provides a method of treating pre-eclampsia (PE) or FGR, comprising administering to a pregnant subject a pharmaceutically effective amount of $H_2S$, an $H_2S$ generating compound or a compound capable of inducing $H_2S$ production in the subject.

The addition of $H_2S$ has been shown to encourage, for example, angio genesis, resulting in the restoration of blood supply to the fetus.

This also means that, for example, pre-term labour may also be treated.

Pre-eclampsia, as described above, is a hypertension syndrome and a major contributor to fetal morbidity. Additionally, fetus may have impaired fetal growth due to the pregnancy induced hypertension. This "impaired fetal growth" produces lower birth weight babies and babies with increased risk of complications later.

The subject is typically a mammal, especially a human.

$H_2S$ may be administered, for example as a gas or solution, such as in a carrier solvent.

Naturally occurring $H_2S$ donating compounds are known. These include allicin from garlic which decomposes to diallyl disulphide and diallyl trisulphide. Sulforaphane is produce by broccoli and erucin is found in rocket (*Eruca Sativa*). These may be provided orally, such as in the form of tablets or capsules.

A number of synthetic $H_2S$ compounds are known. These include GYY4137 (morpholin-4-ium 4 methoxy phenyl (morpholino) phosphinodithiolate) from Cayman Chemical. This has been previously used in rat studies to study $H_2S$ activity by injection intraperitoneally (ip) or intravenously (iv). Lawesson's reagent is another $H_2S$ donor.

SG1002 (Sulfa GENIX Inc) is also a $H_2S$ producing compound and may be used. See also U.S. Pat. No. 8,361, 514 B.

Anethole trithione is also a commonly used $H_2S$ donor. Sodium sulphide in buffer (produced by Ikaria as IK-1001) has been used in clinical trails for reperfusion/injury. Other $H_2S$ generating compounds are disclosed in Bannenberg G. L. and Viera H L A (Expert Opin. Ther. Patents (2009) 19(5) 663-682).

Other compounds are disclosed in the article by Predmore B. L. et al (Antioxidants and Redox Signalling (2012) 17 (1) 119-140), including compounds ADT-OH, TBZ and 4 hydroxyphenylisothiocyanate.

The compound may be ACS-14, AC583, ACS 84, ACS 85, ACS 86 (Lee M, J. Biol Chem (2010) 285, 17318-17328), DATS (diallyl trisulphide), S-diclofenac, sulfane sulphur, thiocysteine, GSH hydropersulphide, GYY4137, SG1002, a $H_2S$-donating derivative of sildenafil (ACS6-Sparatore A et al Expert Rev, Clin. Pharmacol (2011) 4, 109-121), ADT-OH, TBZ and 4-hydroxyphenyl isothiocyanate, thioglycine, 1-thiolysine, 1-thiovaline or salts thereof.

Alternatively, the production of $H_2S$ may be induced in the body for example by inducing CSE production or inducing other enzymes that produce $H_2S$ in the body. For example, statins, such as simvastatin or pravastatin have been found to upregulate CSE production.

The compounds may be introduced by any suitable means, including ip, iv, orally, intrauterine for example as a pessary, or intramuscularly. They may be administered together with one or more pharmaceutically acceptable carriers or excipients. Typical doses may be 10 mmol/kg to 0.01 mol/kg, typically 10 mmol/kg to 0.1 mmol/kg.

Methods of monitoring treatment of pre-eclampsia or impaired fetal growth, comprising measuring the amount of $H_2S$ in a sample of blood, serum or plasma in a subject prior to treatment with $H_2S$, or compound as described above and comparing it to the amount in a sample taken after treatment. Pre-term labour treatment may be similarly monitored.

This allows the amount of $H_2S$ in the body to be subject to ensure that optimal levels of $H_2S$ are provided. The amount of $H_2S$ detected may be detected by techniques generally known in the art, such as the assay method described below.

The subject may have been treated with a compound as described above or alternatively another unrelated anti-PE as anti-impaired fetal growth compound.

The invention will now be described by way of example only with reference to the following Figures:

FIG. 1. CSE expression and $H_2S$ levels in preeclampsia.

Figure 2:
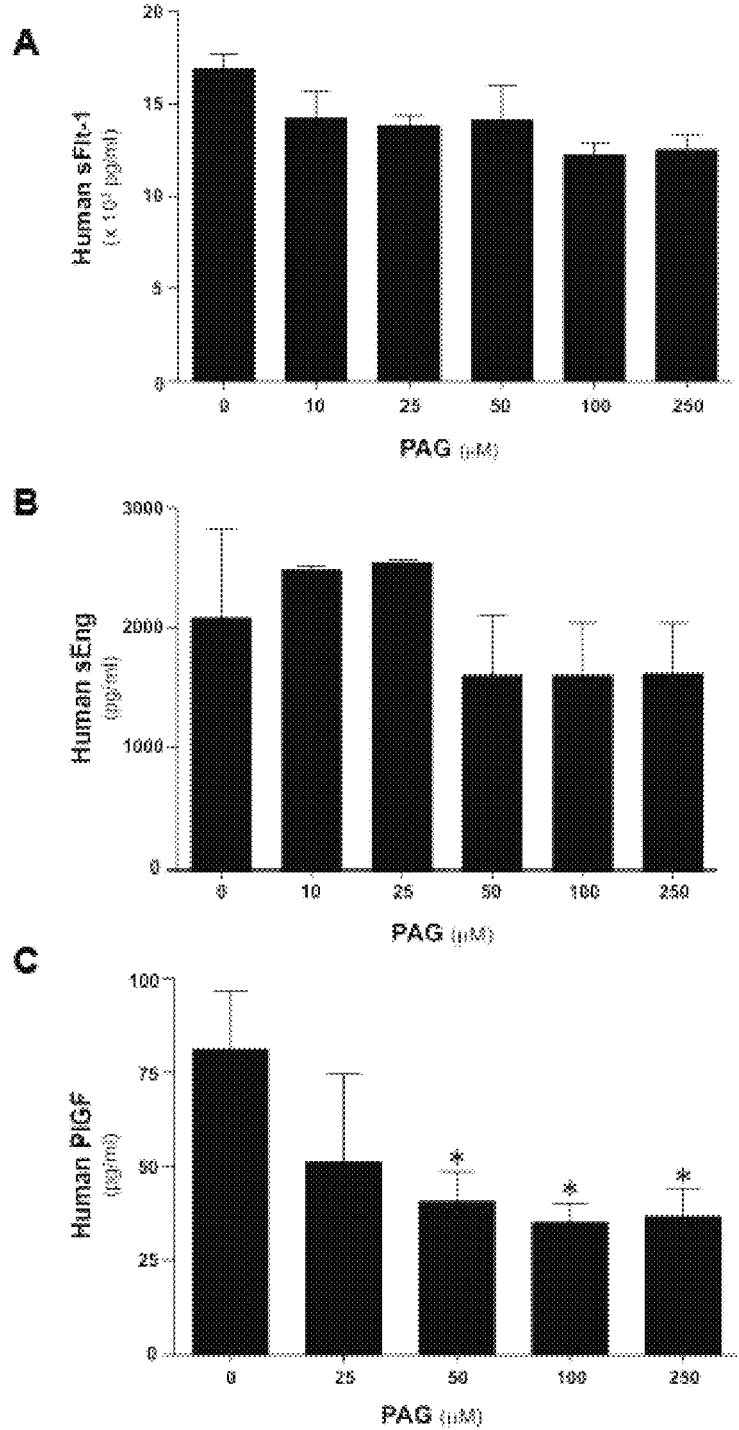

FIG. 2. Effects of CSE inhibition on angiogenesis factor release from human $1^{st}$ trimester placenta.

Figure 3:
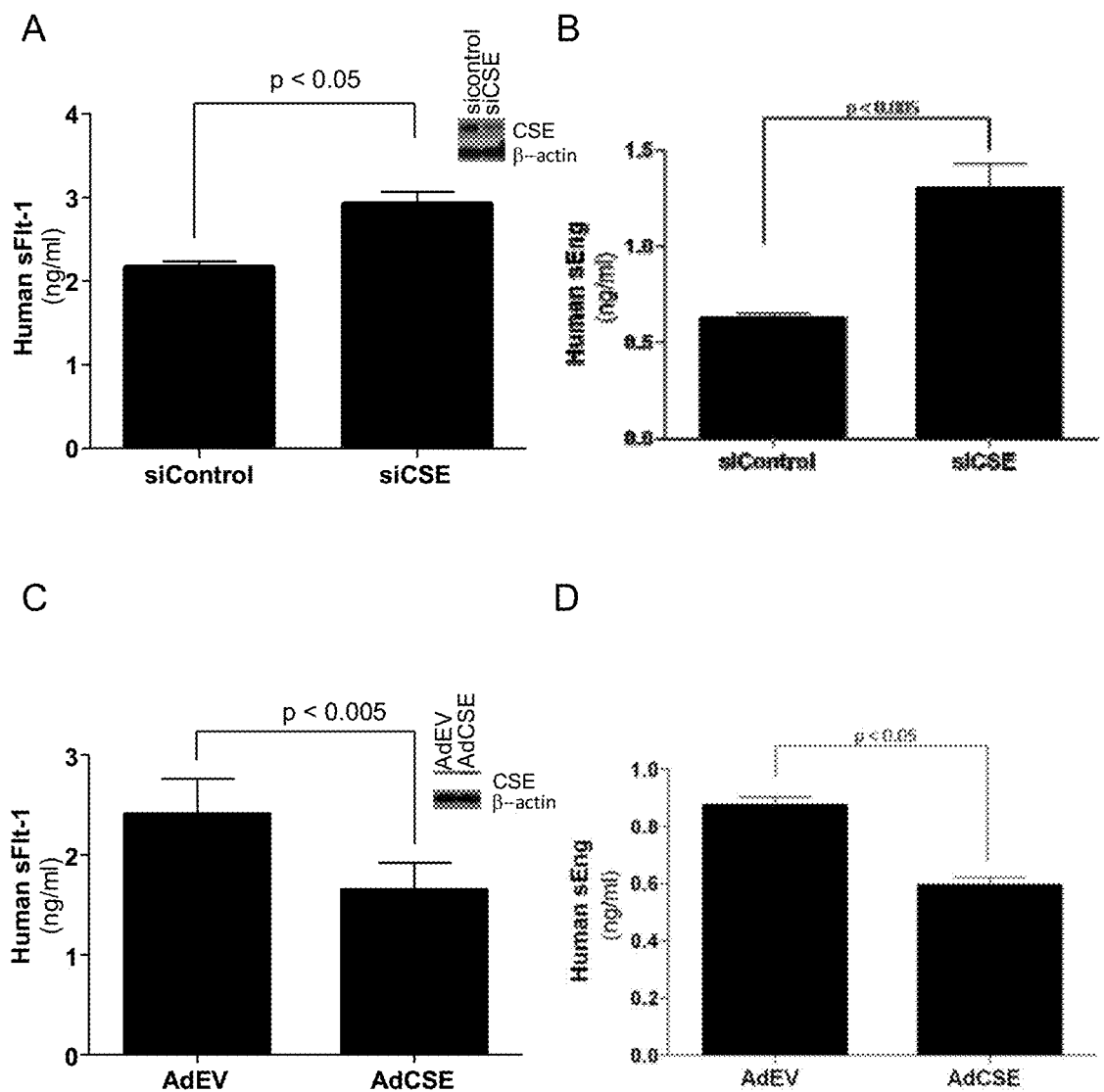

FIG. 3. CSE modulates sFlt-1 and sEng release in endothelial cells.

Figure 4:
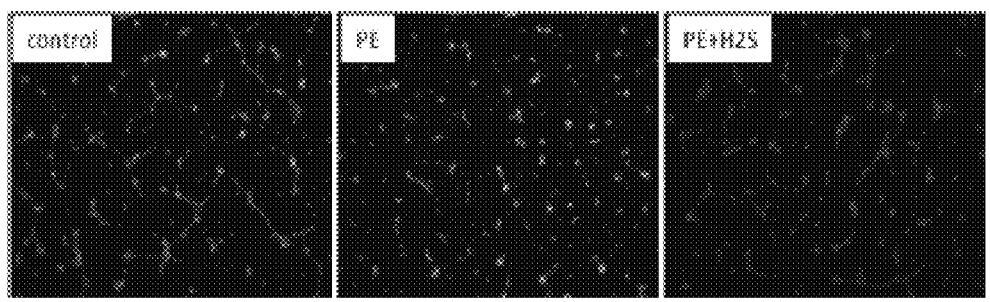
Figure 4:
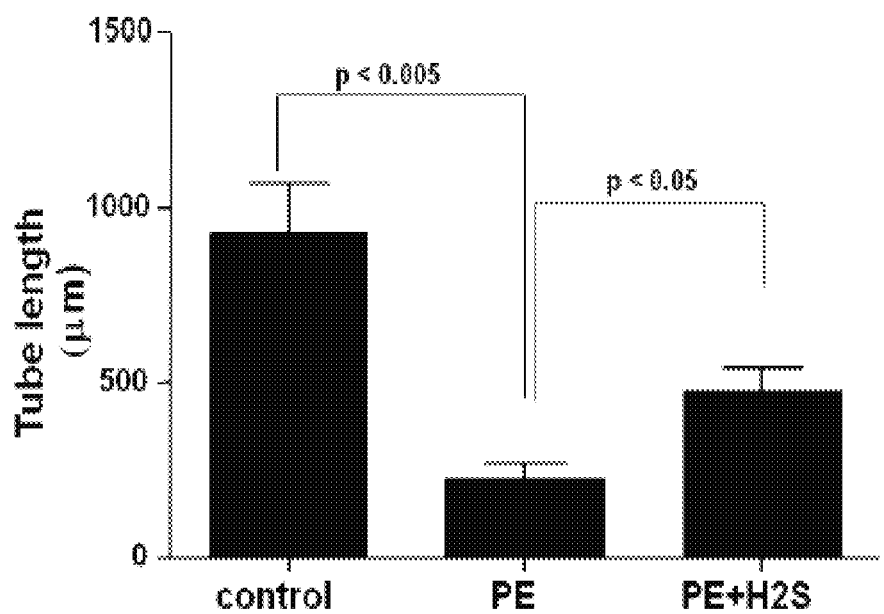

FIG. 4. $H_2S$ rescues preeclamptic sera-induced inhibition of in vitro tube formation.

Figure 5:
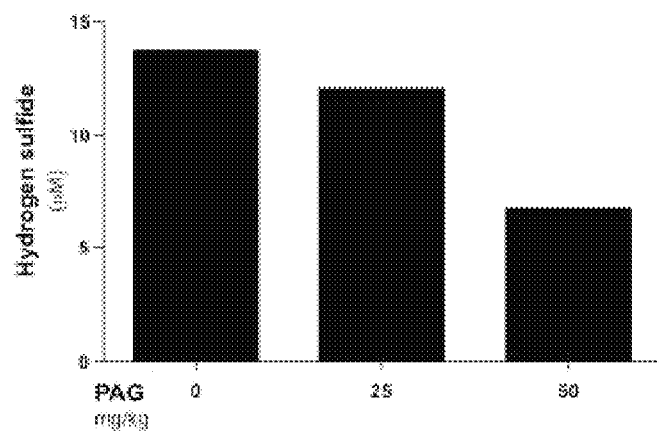
Figure 5:
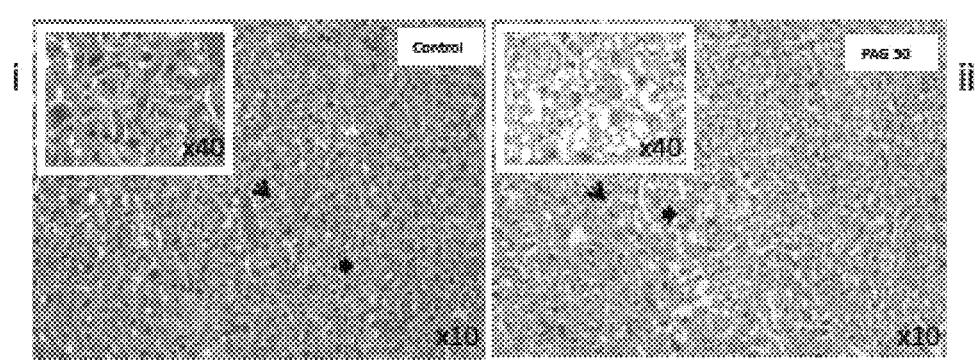
Figure 5:
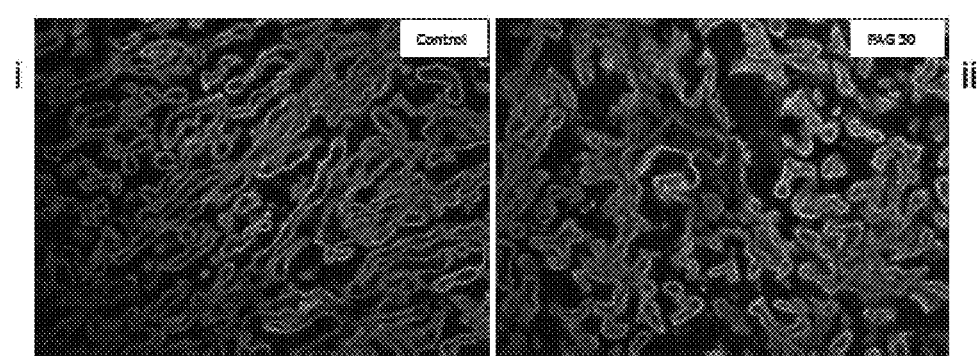

FIG. 5. Inhibition of CSE reduces endogenous circulating $H_2S$ and promotes hypertension and abnormal placental vascularisation in pregnant mice.

Figure 6:
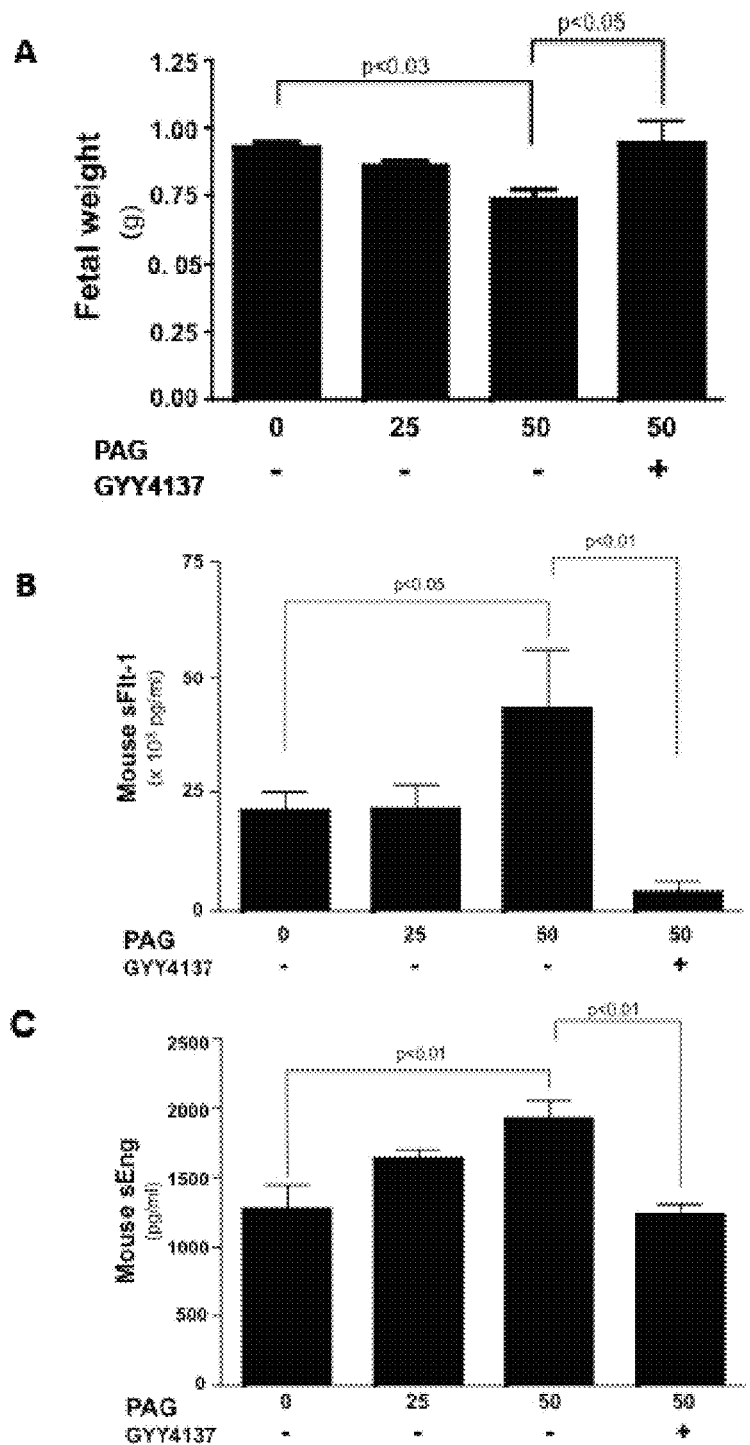

FIG. 6. $H_2S$-generating compound, GYY4137 restored fetal growth and inhibits sFlt-1 and sEng induced by CSE inhibition in pregnant mice.

Figure 7:
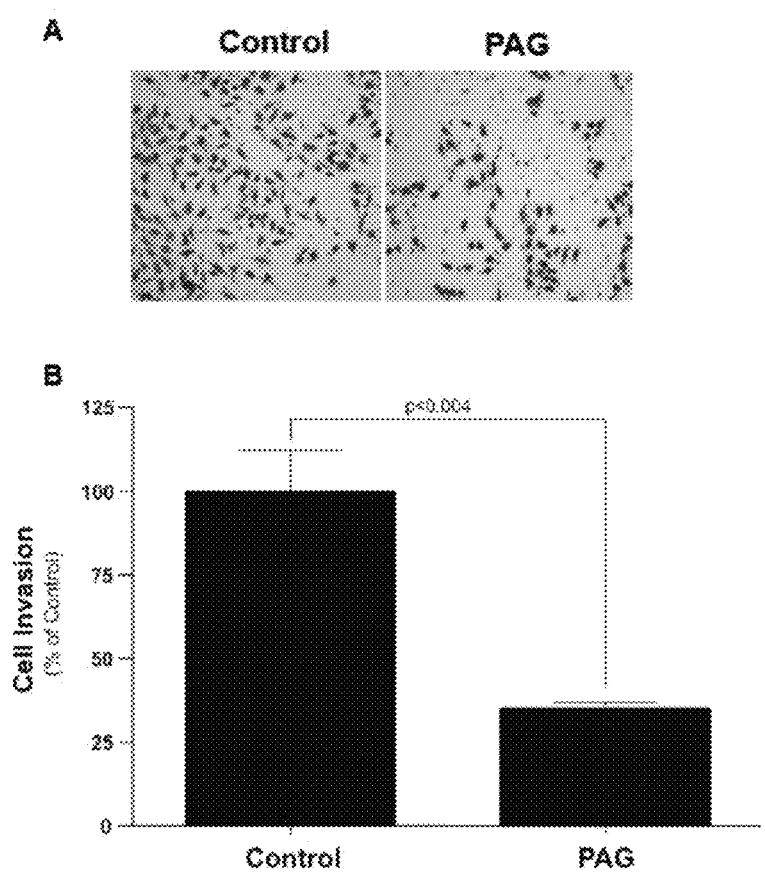

FIG. 7. Effect of inhibition of CSE on trophoblast cell invasion.

Figure 8:
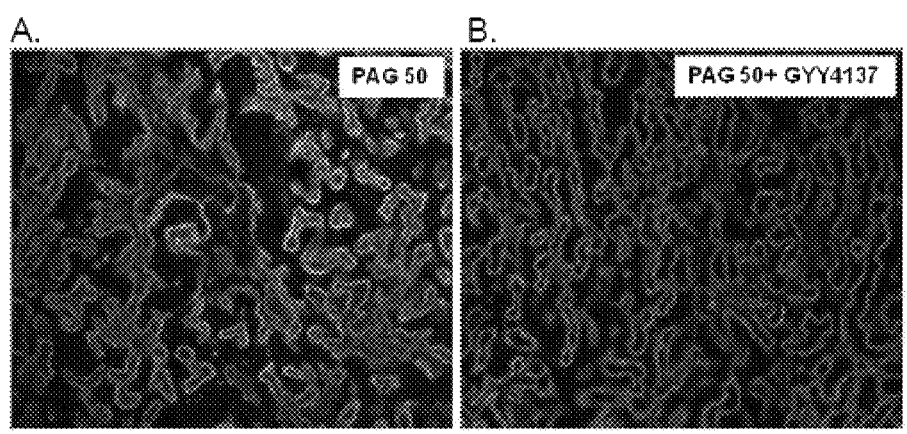

FIG. 8. $H_2S$ donor restores placental vascularisation in pregnant mice.

MATERIALS AND METHODS

Placental Tissue Collection and Preparation

Institutional Ethics Committee approved the blood and tissue collection and written informed consent was obtained. We analysed blood samples from women with singleton pregnancies recruited in the Low- and High-Risk Clinics and Labour and Delivery Unit. All women were followed prospectively from enrolment until delivery. Human placental tissues were collected from pregnancies complicated by preeclampsia and uncomplicated pregnancies delivered by elective Caesarean. Samples of placental tissue were processed for RNA extraction and maternal plasma from the same patients (n=14 PE and n=14 control) were used for analysis. From another set of patients placenta (n=5 PE and n=5 control) was collected for the immunohistochemical study. Preeclampsia was defined as blood pressure>140/90 mm Hg on at least 2 consecutive measurements and maternal proteinuria of at least 300 mg/24 h. First trimester placental tissues (6-9 weeks gestational age) were retrieved from normal pregnancies that had undergone elective termination. Villus explants were prepared as described previously.[29] Briefly, human placental villus explants were incubated with or without PAG for 24 hours, and conditioned media collected and assayed for sFlt-1 or sEng and PlGF.

Animal Experimental Protocol

Eight to ten week old C57/black6 mice were mated. The first day of pregnancy (E0.5) was defined by the presence of a vaginal plug the following morning. Pregnant mice were randomly assigned into four groups: (i) saline (vehicle control), (ii) 25 mg/kg DL-propargylglycine (PAG; Sigma, Poole, U.K.), (iii) 50 mg/kg group PAG and (iv) 50 mg/kg PAG with 0.25 mg/kg of slow-releasing $H_2S$ donor, GYY4137(Sigma). Mice were injected intraperitoneally (i.p.) with saline or PAG from E8.5. Blood pressure was measured by tail cuff-plethysmography. Mice were trained for measurement on alternate days from E4.5. Alternatively, mice were anesthetized by Ketamine/Xylazine cocktail. The carotid artery was isolated and cannulated with a 3-Fr high-fidelity microtip catheter connected to a pressure transducer (Millar Instruments, Houston, Tex., USA). Blood pressure was recorded and averaged over a 10-minute period. On E17.5, after blood pressure measurement and blood sample collection the animals were sacrificed and kidney, liver, and placenta were collected. The un-absorbed fetuses and placentas were counted and weighed.

All experimentation was conducted in accordance with the United Kingdom Animals (Scientific Procedures) Act, 1986 using procedures approved by the University of Edinburgh Ethical Review Committee.

Histopathology

Kidney, liver, and placenta were immersion fixed in 4% paraformaldehyde for 24 hours and processed to paraffin. A series of 5-μm sections were cut and processed for hematoxylin & eosin (H&E) staining.

Cell Culture

Human umbilical vein endothelial cells (HUVEC) were isolated and cultured as previously described.[30] Experiments were performed on third or fourth passage HUVEC.

RNA Interference

To silence human CSE expression, we performed transfection of small-interfering RNA (siRNA) duplex using electroporation (Nucleofector, Amaxa). Control and CSE siRNAs were synthesized by Eurogentec (Cologne, Germany). Knockdown of CSE in HUVEC was confirmed using Western blotting.

Adenoviral Gene Transfer

The recombinant, replication-deficient adenovirus encoding human CSE (AdCSE) and empty vector (AdEV) were purified on CsCl gradients, titered, and stored at −80° C. in viral storage buffer prior to use as described previously.[31] Optimal multiplicity of infection for AdCSE was determined to be 20 IFU/cell by Western blotting using a rabbit anti-CSE antibody (Abcam). AdEV infected HUVEC were used as a negative control.

Enzyme-Linked Immunosorbent Assay

Enzyme-linked immunosorbent assay (ELISA) kits for human and murine soluble Flt-1, soluble endoglin and PlGF were obtained from R&D Systems and performed according to the manufacturer's specifications.

Immunohistochemistry

Serial 3-5-μm sections of formalin-fixed, paraffin-embedded human and murine placental tissue were prepared for immunohistochemistry as previously described.[29] Biotin-labelled isolectin B4, anti-CSE (5 mg/ml) and isotype control were used. The staining was analyzed using a Nikon inverted microscope and an Image Pro Plus image analysis software (Media Cybernetics).

Real-Time Polymerase Chain Reaction (PCR)

Sample preparation and real-time quantitative PCR was performed as described previously.[30] Briefly, mRNA from placental tissue was extracted using TRIzol and DNase-1 digestion/purification on RNAeasy columns (Qiagen), and reverse transcribed with the cDNA Synthesis Kit (Promega). Triplicate cDNA samples and standards were amplified in SensiMix containing SYBR green (Quantace) with primers specific for CSE (GCC-CAG-TTC-CGT-GAA-TCT-AA (SEQ ID NO: 1); CAT-GCT-GAA-GAG-TGC-CCT-TA) (SEQ ID NO: 2)) or β-actin. The mean threshold cycle (CT) for CSE was normalized to β-actin and expressed relative to control.

In Vitro Angiogenesis Assay

The spontaneous formation of capillary-like structures by HUVECs on growth factor-reduced Matrigel (Becton Dickinson, Bedford, Mass.), was used to assess angiogenic potential. HUVECs were treated with plasma samples collected from pregnancies complicated by preeclampsia and uncomplicated pregnancies with or without $H_2S$ donor (NaHS) and incubated at 37° C. for 24 hours. Ninety-six well plates were coated with Matrigel (10 mg/ml) according to the manufacturer's instructions. HUVECs ($1 \times 10^4$ cells/well) were then seeded on Matrigel-coated plates. After incubation for 6 hours, cells were observed with a Nikon inverted microscope and experimental results recorded using the Image Pro-Plus image analysis software (Media Cybernetics).

Measurement of $H_2S$ in Plasma

Citrated blood was obtained from women with uncomplicated pregnancies (n=14) and preeclampsia (n=14) and also from pregnant mice before termination of pregnancy. $H_2S$ levels were measured as described previously with modification.[32] Briefly, 75 µl plasma was mixed with 250 µl of 1% (w/v) zinc acetate and 425 µl water, followed by 250 ml 50% trichloroacetic acid to remove protein. Then 133 µl 20 mM N-dimethyl-p-phenylenediamine sulphate in 7.2 mM HCl and 133 µl 30 µM $FeCl_3$ in 1.2 mM HCl were added to the mixture. After 10 min incubation at room temperature, reaction mixtures were pelleted by centrifugation at 10,000 g (2 minutes). The absorbance of the resulting solution was measured at 670 nm with a spectrophotometer in a 96-well plate. The concentration of $H_2S$ in the solution was calculated against a calibration curve of sodium hydrogen sulfide.

Statistical Analysis

Data are expressed as mean±SEM. The significance of the difference between means was tested by non-parametric Man Whitney t-test. For statistical analysis of changes in clinical samples, one-way ANOVA was used, followed by the Student-Newman-Keuls test as appropriate. An observer blinded to treatment performed the analyses. Statistical significance was set at $p<0.05$.

Results

Placenta CSE Expression is Reduced in Preeclampsia

To investigate whether CSE/$H_2S$ activity is altered in preeclampsia, $H_2S$ was measured in plasma obtained from gestational age-matched control pregnancies and those complicated by preeclampsia. Maternal plasma $H_2S$ levels were significantly reduced in preeclampsia compared with controls group (FIG. 1A). Quantitative real-time PCR revealed that the CSE mRNA expression was significantly reduced in preeclamptic placenta (FIG. 1B) and immunohistochemical staining confirmed that CSE immunoreactivity was dramatically reduced in these samples (FIG. 1C iv) suggesting that the changes in placental CSE levels affect maternal circulating $H_2S$ levels. Expressed of CSE was located in the trophoblast, the endothelium and the mesenchymal cells within the core of the chorionic villus. The latter are possibly the Hofbauer cells, which are of mesenchymal origin (FIG. 1C iii). Clinical characteristics of the study patients are described in Table 1.

Inhibition of CSE Activity Reduces PlGF Release in Placental Explants

Angiogenic factors produced by placenta are important in regulating placental vascular development.[33] Imbalance of pro- and anti-angiogenic factors generated by the placenta[29] may account for the widespread maternal endothelial dysfunction in preeclampsia.[34] To investigate whether reduced levels of CSE has any effect on the production of placental angiogenic factor production, sFlt-1, sEng, and PlGF levels were measured in conditioned medium from first trimester human placental explants in the presence of increasing concentration of CSE inhibitor PAG over 24 hours. While the levels of sFlt-1 and sEng remained unchanged by the inhibition of CSE activity, PlGF production was significantly reduced (FIG. 2). This suggests that reduction in endogenous $H_2S$ may alter the placental sFlt-1/PlGF ratio, which has been implicated in the pathogenesis of preeclampsia.[18, 29] In addition, a significant reduction ($p<0.01$) in cell invasion was observed when first trimester trophoblast cells (HTR-8/SVneo) were incubated with the CSE specific inhibitor PAG (50 µM) compared with the vehicle control (Supplemental FIGS. S1A and S1B), suggesting that lack of CSE activity may affect placental perfusion which is essential for establishing normal pregnancy.

CSE Modulates sFlt-1 and sEng Release in Endothelial Cells

Although placenta has been considered to be the main source of sFlt-1 and sEng release in preeclampsia patients, some studies have shown that levels of sFlt-1 remained higher in women with a history of preeclampsia compared with those without preeclampsia an average of 18 months postpartum[35, 36] suggesting that other antiangiogenic milieu are involved in the process. To investigate whether CSE affects sFlt-1 and sEng release in endothelial cells, CSE expression was modulated by siRNA or adenovirus in HUVECs. Down-regulation of CSE increased both sFlt-1 and sEng release (FIG. 3A, 3B) while over-expression of CSE inhibited sFlt-1 and sEng release by HUVECs (FIG. 3C, 3D). These data further support the concept that loss of CSE activity may contribute to the pathogenesis of preeclampsia.

$H_2S$ Partially Rescues Preeclamptic Plasma-Induced Inhibition of In Vitro Tube Formation It has been demonstrated that excess sFlt-1 generated by preeclamptic placenta inhibits in vitro endothelial tube formation and removal of sFlt-1 from preeclampsia samples restores angiogenesis.[29] To assess whether $H_2S$ can reverse the anti-angiogenic effects of preeclampsia, plasma from normotensive or preeclamptic women was added to HUVEC grown on growth factor-reduced Matrigel in the presence of 100 mM NaHS, a $H_2S$ donor, and in vitro tube formation assay performed. Consistence with earlier findings, preeclamptic plasma inhibited capillary tube network formation compare with normal control sera (FIG. 4). More importantly, NaHS, a $H_2S$ donor, partially restored the ability of HUVECs to form tube-like structure (FIG. 4A, 4B).

Blocking Endogenous $H_2S$ Causes Hypertension and Abnormal Placental Vascularisation in Pregnant Mice We predicted that inhibition of CSE in vivo would cause a preeclampsia-like syndrome in pregnant mice. Three groups (5-8/group) of pregnant C57Bl6/J mice were treated daily with vehicle or 25 mg/kg PAG or 50 mg/kg PAG from E8.5 to E16.5. After 8 days of treatment, plasma was pooled from all animals in each treatment group, and pooled $H_2S$ levels were measured. PAG caused a dose-dependent decrease in circulating $H_2S$ levels. The higher dose reduced plasma $H_2S$ levels by approximately 50% (FIG. 5A). In consistence of these data, we found that the mean blood pressure in high dose PAG treated group was significant higher compared with vehicle control (74.40±4.61 and 64.74±2.04) (Table 2). Although renal pathological changes such as proteinuria was not noted in our PAG treated animals (Table 2), liver damage represented by increased level of circulating liver enzyme aspartate transaminas (AST) was found in PAG-treated animals (Table 2). These date suggest that lack of CSE activity may cause non-proteinuric preeclampsia. Interestingly, all the changes of PAG-treated pregnant mice were abrogated by a slow releasing, $H_2S$-generating compound GYY4137 (0.25 mg/kg) treatment (Table 2). Blinded histological analysis of placental sections showed that the maternal blood space in the labyrinth zone appeared larger in 50 mg/kg PAG-treated animals than in vehicle controls (FIG. 5B). The labyrinth zone consists of cells of trophoblast and mesodermal origin that together undergo branching morphogenesis, resulting in a large surface area for nutrient and gas exchange between the mother and fetus.

The maternal blood space is lined by trophoblast. During placental development, this space becomes progressively more finely divided.[37, 38] Using isolectin B4 to highlight the fetal endothelial cell,[39] we compared the anatomical features of the labyrinth zone in vehicle and 50 mg/kg PAG-treated mice. In control mice, the labyrinth appeared as organised fetal vessels with well-developed branching morphogenesis. In contrast, the fetal vasculature of the placenta in PAG-treated animals was observed as irregular branching (FIG. 5C) and maternal vasculature appear to be dilated. The morphology of placenta from PAG-treated animals suggests a placental vascular defect due to inhibition of CSE activity. This defect was also restored by $H_2S$ donor GYY4137 treatment (FIG. S2).

The Effects of Inhibition of CSE Activity on Fetal Outcomes and sFlt-1 and sEng Production Fetal weight was significantly decreased in mice that received the higher dose of PAG (FIG. 6A). This could be explained by placental vascular defect induced by inhibition of CSE activity. GYY4137, at 0.25 mg/kg restored fetal growth compromised by the CSE inhibitor (FIG. 6A). Furthermore, GYY4137 inhibited the plasma levels of sFlt-1 and sEng induced by CSE inhibition (FIGS. 6B and 6C) in mice treated with 50 mg/kg PAG (FIGS. 5B and 5C). Plasma PlGF was below the detection limit of the assay. These data suggest that inhibition of CSE activity alters maternal angiogenic balance and $H_2S$ can help to restore normal angiogenic status.

Discussion

Chronic administration of a CSE inhibitor leads to reduced $H_2S$ and increased blood pressure in rats.[7] Thus it is plausible that a reduction in the circulating $H_2S$ level may contribute to hypertension in preeclampsia. In this study we provide evidence that preeclampsia is associated with reduced circulating $H_2S$, which is accompanied by downregulation of placental CSE, the key enzyme responsible for the generation of endogenous $H_2S$. Furthermore, the inhibition of CSE in pregnant mice induces hypertension, increases sFlt-1 and sEng levels and causes placental abnormalities. This is due to inhibition of $H_2S$ production as a slow releasing, $H_2S$-generating compound, GYY4137, inhibited circulating sFlt-1 and sEng levels and restored fetal growth compromised by CSE inhibition. These findings indicate that a dysfunctional CSE/$H_2S$ pathway may contribute to the pathogenesis of preeclampsia.

$H_2S$ is a vasorelaxant factor that acts through $K_{ATP}$ channels causing smooth muscle relaxation[1, 40] Studies using mice genetically deficient in CSE demonstrated that this enzyme is the major source of $H_2S$ in both the vasculature and the peripheral tissues.[9] Recently, CSE expression was found in the placenta and pregnant myometrium and it was shown to play a role in uterine contractility.[27, 28] In this study, placental CSE levels were dramatically reduced in preeclamptic patients compared with normotensive controls. A recent study also showed similar pattern in CSE in preeclamptic placenta.[41] These findings suggest that lack of the CSE leads to the reduction in circulating $H_2S$.

Angiogenic imbalance has been highlighted as the prime culprit in preeclampsia over systemic inflammation.[42, 43] In this study, CSE was found to be a negative regulator of anti-angiogenic factors, sFlt-1 and sEng, in endothelial cells, suggesting that dysregulation of CSE may contribute to the lasting endothelial dysfunction and an elevated risk of cardiovascular disease in women with a history of preeclampsia. In addition, the decrease in VEGF and PlGF activity in preeclampsia is believed to be the result of excess sFlt-1.[16, 18] As sFlt-1 levels are comparable to healthy controls during the first trimester of pregnancy, this theory does not explain why the circulating levels of PlGF are low in early pregnancy in women who subsequently develop preeclampsia.[44] Our findings that inhibition of endogenous placental $H_2S$ generation by CSE inhibitor attenuates the production of PlGF in first trimester placental explants provides a possible explanation and a new hypothesis for testing: namely, the decrease in PlGF expression in early pregnancy is due to loss or reduction in the enzymes producing $H_2S$. Furthermore, inhibition of CSE activity abolished the invasion of first-trimester extravillus trophoblast cells suggesting that dysregulation of CSE/$H_2S$ pathway may not only change the balance of placental pro- and anti-angiogenesis factors, but also dysregulate maternal spiral artery remodeling and placental development.

In pregnant mice, CSE inhibition reduced endogenous $H_2S$ and this was accompanied by an increase in blood pressure, and liver damage without renal pathological changes such as proteinuria and glomerular endotheliosis, a syndrome similar to non-proteinuric preeclampsia. However, it also suggests that other factors are also involved in the full spectrum of preeclampsia. Preeclampsia is also strongly associated with placental abnormalities including compromised villus volume and surface area, as well as reduced placental vascularisation.[15, 45] In the PAG-treated mice, the fetal labyrinth showed impaired branching morphogenesis, indicating endogenous $H_2S$ is required for placental development.

Impaired placental perfusion and suboptimal oxygen and nutrient diffusion has been reported to occur as a result of inappropriate labyrinth vascularisation with altered patterning, branching and dilation.[46] Blood pressure, liver function and fetal weight compromised by PAG-treatment were rescued by the slow releasing, $H_2S$-generating compound, GYY4137, demonstrating that the effects of CSE inhibitor were due to inhibition of $H_2S$ production. These results imply that endogenous $H_2S$ is required for healthy placental vasculature to support fetal wellbeing.

Clinical Perspective

The present study shows that dysregulation of CSE/$H_2S$ pathway is associated with preeclampsia and inhibition of CSE activity in pregnant mice produces some of the features of preeclampsia, including hypertension and impaired fetal outcomes. These findings support the concept that $H_2S$ is an important regulator of the placental vasculature development, a deficiency of which appears to be associated with preeclampsia and fetal growth restriction.

Supplemental Methods

Trophablast Cell Invasion Assay

The human extravillus trophoblast (EVT) cell line HTR-8/SVneo was a kind gift from Professor Charles H. Graham, Queen's University, Kingston, Ontario, Canada. The invasion assay was performed as described previously, with modification.30 Briefly, HTR-8/SVneo (50,000) cells treated with or without PAG were placed in the upper chamber of Matrigel-coated (1 mg/ml) transwell inserts (8 m pore, Falcon, BD, UK) and housed in a 24-well plate. The cells were allowed to invade through the reconstituted extracellular matrix for 24 h in the presence or absence of 50 μM PAG (n=3). Trophoblast cells located on the undersurface of the transwell membrane were fixed with ice-cold methanol and stained with hematoxylin, and brightfield images were obtained with Nikon inverted microscope and Image Pro Plus image analysis software (Media Cybernetics).

Immunohistochemistry

Serial 3-5-μm sections of formalin-fixed, paraffin-embedded murine placental tissue were prepared for immunohistochemistry as previously described[48]. Biotin-labelled isolectin B4, were used. The staining was analyzed using a Nikon inverted microscope and an Image Pro Plus image analysis software (Media Cybernetics).

FIG. 7. Effect of Inhibition of CSE on Trophoblast Cell Invasion.

Transwell migration assays of HTR-8/SVneo cells in the presence of 50 μM of PAG were performed as described in Methods. (A) Migrated HTR-8/SVneo were stained with hematoxylin, and brightfield images were captured. (B) Cell numbers were counted, and results are expressed as a percentage of the control (n=3).

FIG. 8. $H_2S$ Donor Restores Placental Vascularisation in Pregnant Mice.

Placental tissue from mice received either (A) PAG 50 mg/kg or (B) PAG 50 mg/kg plus GYY4137 injection were sectioned and stained with Isolectin B4 to visualize haemotrichorial labyrinth zone.

REFERENCES

1. Zhao W, Zhang J, Lu Y, Wang R. The vasorelaxant effect of H(2)S as a novel endogenous gaseous K(ATP) channel opener. *Embo J.* 2001; 20(21):6008-6016.
2. Papapetropoulos A, Pyriochou A, Altaany Z, Yang G, Marazioti A, Zhou Z, Jeschke M G, Branski L K, Hemdon D N, Wang R, Szabo C. Hydrogen sulfide is an endogenous stimulator of angiogenesis. *Proc Natl Acad Sci USA.* 2009; 106(51):21972-21977.
3. Zanardo R C, Brancaleone V, Distrutti E, Fiorucci S, Cirino G, Wallace J L. Hydrogen sulfide is an endogenous modulator of leukocyte-mediated inflammation. *Faseb J.* 2006; 20(12):2118-2120.
4. Blackstone E, Roth M B. Suspended animation-like state protects mice from lethal hypoxia. *Shock.* 2007; 27(4): 370-372.
5. Elrod J W, Calvert J W, Morrison J, Doeller J E, Kraus D W, Tao L, Jiao X, Scalia R, Kiss L, Szabo C, Kimura H, Chow C W, Lefer D J. Hydrogen sulfide attenuates myocardial ischemia-reperfusion injury by preservation of mitochondrial function. *Proc Natl Acad Sci USA.* 2007; 104(39):15560-15565.
6. Kabil O, Vitvitsky V, Xie P, Banerjee R. The quantitative significance of the transsulfuration enzymes for $H_2S$ production in murine tissues. *Antioxid Redox Signal.* 2011; 15(2):363-372.
7. Yan H, Du J, Tang C. The possible role of hydrogen sulfide on the pathogenesis of spontaneous hypertension in rats. *Biochem Biophys Res Commun.* 2004; 313(1):22-27.
8. Yanfei W, Lin S, Junbao D, Chaoshu T. Impact of L-arginine on hydrogen sulfide/cystathionine-gamma-lyase pathway in rats with high blood flow-induced pulmonary hypertension. *Biochem Biophys Res Commun.* 2006; 345(2):851-857.
9. Yang G, Wu L, Jiang B, Yang W, Qi J, Cao K, Meng Q, Mustafa A K, Mu W, Zhang S, Snyder S H, Wang R. $H_2S$ as a physiologic vasorelaxant: hypertension in mice with deletion of cystathionine gamma-lyase. *Science.* 2008; 322(5901):587-590.
10. Li L, Moore P K. Putative biological roles of hydrogen sulfide in health and disease: a breath of not so fresh air? *Trends Pharmacol Sci.* 2008; 29(2):84-90.
11. Banerjee R. Hydrogen sulfide: redox metabolism and signaling. *Antioxid Redox Signal.* 2011; 15(2):339-341.
12. Hogberg U. The World Health Report 2005: "make every mother and child count"-including Africans. *Scand J Public Health.* 2005; 33(6):409-411.
13. Homer C S, Brown M A, Mangos G, Davis G K. Non-proteinuric pre-eclampsia: a novel risk indicator in women with gestational hypertension. *J Hypertens.* 2008; 26(2):295-302.
14. Brosens I A, Robertson W B, Dixon H G. The role of the spiral arteries in the pathogenesis of preeclampsia. *Obstet Gynecol Annu.* 1972; 1:177-191.
15. Egbor M, Ansari T, Morris N, Green C J, Sibbons P D. Morphometric placental villous and vascular abnormalities in early- and late-onset pre-eclampsia with and without fetal growth restriction. *Bjog.* 2006; 113(5):580-589.
16. Ahmed A, Cudmore M J. Can the biology of VEGF and haem oxygenases help solve pre-eclampsia? *Biochem Soc Trans.* 2009; 37(Pt 6):1237-1242.
17. Maynard S E, Karumanchi S A. Angiogenic factors and preeclampsia. *Semin Nephrol.* 2011; 31(1):33-46.
18. Levine R J, Maynard S E, Qian C, Lim K H, England L J, Yu K F, Schisterman E F, Thadhani R, Sachs B P, Epstein F H, Sibai B M, Sukhatme V P, Karumanchi S A. Circulating angiogenic factors and the risk of preeclampsia. *N Engl J Med.* 2004; 350(7):672-683.
19. Levine R J, Lam C, Qian C, Yu K F, Maynard S E, Sachs B P, Sibai B M, Epstein F H, Romero R, Thadhani R, Karumanchi S A. Soluble endoglin and other circulating antiangiogenic factors in preeclampsia. *N Engl J Med.* 2006; 355(10):992-1005.
20. Torry D S, Wang H S, Wang T H, Caudle M R, Torry R J. Preeclampsia is associated with reduced serum levels of placenta growth factor. *Am J Obstet Gynecol.* 1998; 179(6 Pt 1):1539-1544.
21. Taylor R N, Grimwood J, Taylor R S, McMaster M T, Fisher S J, North R A. Longitudinal serum concentrations of placental growth factor: evidence for abnormal placental angiogenesis in pathologic pregnancies. *Am J Obstet Gynecol.* 2003; 188(1):177-182.

22. Levine R J, Thadhani R, Qian C, Lam C, Lim K H, Yu K F, Blink A L, Sachs B P, Epstein F H, Sibai B M, Sukhatme V P, Karumanchi S A. Urinary placental growth factor and risk of preeclampsia. *Jama.* 2005; 293(1):77-85.
23. Buhimschi C S, Norwitz E R, Funai E, Richman S, Guller S, Lockwood C J, Buhimschi I A. Urinary angiogenic factors cluster hypertensive disorders and identify women with severe preeclampsia. *Am J Obstet Gynecol.* 2005; 192(3):734-741.
24. Savvidou M D, Noori M, Anderson J M, Hingorani A D, Nicolaides K H. Maternal endothelial function and serum concentrations of placental growth factor and soluble endoglin in women with abnormal placentation. *Ultrasound Obstet Gynecol.* 2008; 32(7):871-876.
25. Foidart J M, Munaut C, Chantraine F, Akolekar R, Nicolaides K H. Maternal plasma soluble endoglin at 11-13 weeks' gestation in pre-eclampsia. *Ultrasound Obstet Gynecol.* 2010; 35(6):680-687.
26. Noori M, Donald A E, Angelakopoulou A, Hingorani A D, Williams D J. Prospective study of placental angiogenic factors and maternal vascular function before and after preeclampsia and gestational hypertension. *Circulation.* 2010; 122(5):478-487.
27. Patel P, Vatish M, Heptinstall J, Wang R, Carson R J. The endogenous production of hydrogen sulphide in intrauterine tissues. *Reprod Biol Endocrinol.* 2009; 7:10.
28. You X J, Xu C, Lu J Q, Zhu X Y, Gao L, Cui X R, Li Y, Gu H, Ni X. Expression of cystathionine beta-synthase and cystathionine gamma-lyase in human pregnant myometrium and their roles in the control of uterine contractility. *PLoS ONE.* 2011; 6(8):e23788.
29. Ahmad S, Ahmed A. Elevated placental soluble vascular endothelial growth factor receptor-1 inhibits angiogenesis in preeclampsia. *Circ Res.* 2004; 95(9):884-891.
30. Ahmad S, Hewett P W, Wang P, Al-Ani B, Cudmore M, Fujisawa T, Haigh J J, le Noble F, Wang L, Mukhopadhyay D, Ahmed A. Direct evidence for endothelial vascular endothelial growth factor receptor-1 function in nitric oxide-mediated angiogenesis. *Circ Res.* 2006; 99(7):715-722.
31. Cudmore M, Ahmad S, Al-Ani B, Fujisawa T, Coxall H, Chudasama K, Devey L R, Wigmore S J, Abbas A, Hewett P W, Ahmed A. Negative regulation of soluble Flt-1 and soluble endoglin release by heme oxygenase-1. *Circulation.* 2007; 115(13):1789-1797.
32. Zhuo Y, Chen P F, Zhang A Z, Zhong H, Chen C Q, Zhu Y Z. Cardioprotective effect of hydrogen sulfide in ischemic reperfusion experimental rats and its influence on expression of surviving gene. *Biol Pharm Bull.* 2009; 32(8):1406-1410.
33. Reynolds L P, Redmer D A. Utero-placental vascular development and placental function. *J Anim Sci.* 1995; 73(6):1839-1851.
34. Maynard S E, Min J Y, Merchan J, Lim K H, Li J, Mondal S, Libermann T A, Morgan J P, Sellke F W, Stillman I E, Epstein F H, Sukhatme V P, Karumanchi S A. Excess placental soluble fms-like tyrosine kinase 1 (sFlt1) may contribute to endothelial dysfunction, hypertension, and proteinuria in preeclampsia. *J Clin Invest.* 2003; 111(5):649-658.
35. Saxena A R, Karumanchi S A, Brown N J, Royle C M, McElrath T F, Seely E W. Increased sensitivity to angiotensin II is present postpartum in women with a history of hypertensive pregnancy. *Hypertension.* 2010; 55(5):1239-1245.
36. Wolf M, Hubel C A, Lam C, Sampson M, Ecker J L, Ness R B, Rajakumar A, Daftary A, Shakir A S, Seely E W, Roberts J M, Sukhatme V P, Karumanchi S A, Thadhani R. Preeclampsia and future cardiovascular disease: potential role of altered angiogenesis and insulin resistance. *J Clin Endocrinol Metab.* 2004; 89(12):6239-6243.
37. Adamson S L, Lu Y, Whiteley K J, Holmyard D, Hemberger M, Pfarrer C, Cross J C. Interactions between trophoblast cells and the maternal and fetal circulation in the mouse placenta. *Dev Biol.* 2002; 250(2):358-373.
38. Watson E D, Cross J C. Development of structures and transport functions in the mouse placenta. *Physiology* (Bethesda). 2005; 20:180-193.
39. Ohlsson R, Falck P, Hellstrom M, Lindahl P, Bostrom H, Franklin G, Ahrlund-Richter L, Pollard J, Soriano P, Betsholtz C. PDGFB regulates the development of the labyrinthine layer of the mouse fetal placenta. *Dev Biol.* 1999; 212(1):124-136.
40. Tang G, Wu L, Wang R. The effect of hydroxylamine on KATP channels in vascular smooth muscle and underlying mechanisms. *Mol Pharmacol.* 2005; 67(5):1723-1731.
41. Holwerda K M, Bos E M, Rajakumar A, Ris-Stalpers C, van Pampus M G, Timmer A, Erwich J J, Faas M M, van Goor H, Lely A T. Hydrogen sulfide producing enzymes in pregnancy and preeclampsia. *Placenta.* 2012; 33(6): 518-521.
42. Ramma W, Ahmed A. Is inflammation the cause of pre-eclampsia? *Biochem Soc Trans.* 2011; 39(6): 1619-1627.
43. Ramma W, Buhimschi I A, Zhao G, Dulay A T, Nayeri U A, Buhimschi C S, Ahmed A. The elevation in circulating anti-angiogenic factors is independent of markers of neutrophil activation in preeclampsia. *Angiogenesis.* 2012; 15(3):333-340.
44. Thadhani R, Mutter W P, Wolf M, Levine R J, Taylor R N, Sukhatme V P, Ecker J, Karumanchi S A. First trimester placental growth factor and soluble fms-like tyrosine kinase 1 and risk for preeclampsia. *J Clin Endocrinol Metab.* 2004; 89(2):770-775.
45. Chen C P. Placental abnormalities and preeclampsia in trisomy 13 pregnancies. Taiwan *J Obstet Gynecol.* 2009; 48(1):3-8.
46. Cross J C, Simmons D G, Watson E D. Chorioallantoic morphogenesis and formation of the placental villous tree. *Ann N Y Acad Sci.* 2003; 995:84-93.
47. Damsky C H, Fitzgerald M L, Fisher S J. Distribution patterns of extracellular matrix components and adhesion receptors are intricately modulated during first trimester cytotrophoblast differentiation along the invasive pathway, in vivo. *J Clin Invest.* 1992; 89(1):210-222.
48. Ahmad S, Ahmed A. Elevated placental soluble vascular endothelial growth factor receptor-1 inhibits angiogenesis in preeclampsia. *Circ Res.* 2004; 95(9):884-891.

The invention claimed is:

1. A method for treating pre-eclampsia or fetal growth restriction in a host animal, the method comprising (a) measuring an amount of $H_2S$ in a sample from the host animal; and (b) administering a therapeutically effective amount of a compound capable of generating hydrogen sulfide to the host animal.

2. The method of claim 1 wherein the compound is ACS14, ACS583, ACS84, ACS85, ACS86, DATS (diallyl trisulfide), S-diclofenac, sulfane, sulfur, thiocysteine, GSH hydropersulfide, GYY4137, SG1002, a $H_2S$-donating derivative of sildenafil, ADT-OH, TBZ, 4-hydroxyphenyl isothiocyanate, thioglycine, 1-thiolysine, 1-thiovaline, $H_2S$-Sartans, or $H_2S$-L-DOPA or a salt of any of the foregoing, or a combination of any of the foregoing.

3. The method of claim 1 comprising administering GYY4137.

4. The method of claim 3 for treating pre-eclampsia.

5. The method of claim 3 for treating fetal growth restriction.

6. The method of claim 1 wherein the compound is ACS14, ACS583, ACS84, ACS85, or ACS86, or a salt of any of the foregoing, or a combination of any of the foregoing.

7. The method of claim 6 for treating pre-eclampsia.

8. The method of claim 6 for treating fetal growth restriction.

9. The method of claim 1 comprising measuring the amount of $H_2S$ in a sample of blood, serum, or plasma from the host.

10. The method of claim 1 comprising administering ACS14 or ADT-OH or a salt thereof.

11. The method of claim 10 for treating pre-eclampsia.

12. The method of claim 10 for treating fetal growth restriction.

13. The method of claim 11 comprising administering ACS14.

14. The method of claim 12 comprising administering ACS14.

15. The method of claim 1 wherein the amount of $H_2S$ is measured from CSE expression.

16. The method of claim 1 wherein the amount of $H_2S$ is measured from sFlt-1 expression.

17. The method of claim 1 wherein the amount of $H_2S$ is measured from PlGF production.

18. The method of claim 1 wherein the amount of $H_2S$ is measured from sEng production.

19. The method of claim 1 wherein the amount of $H_2S$ is measured from inhibition level of VEGF.

20. The method of claim 1 wherein the amount of $H_2S$ is measured from inhibition level of PlGF.

* * * * *

UNITED STATES PATENT AND TRADEMARK OFFICE
CERTIFICATE OF CORRECTION

PATENT NO. : 10,821,122 B2  
APPLICATION NO. : 16/229173  
DATED : November 3, 2020  
INVENTOR(S) : Asif Ahmed Page 1 of 1

It is certified that error appears in the above-identified patent and that said Letters Patent is hereby corrected as shown below:

Column 13, In Claim 2, Line 26, "S-diclofenac, sulfane, sulfur, thiocysteine," should read -- S-diclofenac, sulfane, thiocysteine, --.

Signed and Sealed this  
Twenty-second Day of December, 2020

Andrei Iancu  
*Director of the United States Patent and Trademark Office*

SEQUENCE LISTING

<160> NUMBER OF SEQ ID NOS: 2

<210> SEQ ID NO 1
<211> LENGTH: 20
<212> TYPE: DNA

```
<213> ORGANISM: Homo sapiens

<400> SEQUENCE: 1
gcccagttcc gtgaatctaa                                           20

<210> SEQ ID NO 2
<211> LENGTH: 20
<212> TYPE: DNA
<213> ORGANISM: Homo sapiens

<400> SEQUENCE: 2
catgctgaag agtgcccttaa                                          20
```